United States Patent [19]
Richelsoph

[11] Patent Number: 5,466,261
[45] Date of Patent: Nov. 14, 1995

[54] NON-INVASIVE EXPANDABLE PROSTHESIS FOR GROWING CHILDREN

[75] Inventor: Marc E. Richelsoph, Cordova, Tenn.

[73] Assignee: Wright Medical Technology, Inc., Arlington, Tenn.

[21] Appl. No.: 979,508

[22] Filed: Nov. 19, 1992

[51] Int. Cl.$^6$ .................. A61F 2/28; A61F 5/04
[52] U.S. Cl. .................. 623/16; 606/60; 606/62; 606/63
[58] Field of Search .................. 623/11, 16, 18; 606/105

[56] References Cited

U.S. PATENT DOCUMENTS

| | | | |
|---|---|---|---|
| 4,502,160 | 3/1985 | Moore et al. | 3/1.9 |
| 4,854,428 | 8/1989 | Horvath | 623/18 X |
| 4,892,546 | 1/1990 | Kotz et al. | 623/16 X |
| 5,071,435 | 12/1991 | Fuchs et al. | 623/16 |
| 5,281,226 | 1/1994 | Dauydov et al. | 623/16 X |

FOREIGN PATENT DOCUMENTS

| | | | |
|---|---|---|---|
| 0409159 | 6/1992 | European Pat. Off. | 623/18 |
| 2666221 | 3/1992 | France | 623/16 |

Primary Examiner—David Isabella

[57] ABSTRACT

An adjustable length prosthetic implant includes a stem having a rod portion, the rod portion including a first end portion adapted for connection to a bone and a second end portion including a piston reciprocable in a sleeve. The sleeve includes a closed end and an inner chamber extending to an opposite open end and defining an axial dimension. The chamber contains the piston for sliding movement therethrough and extension of the first end portion of the stem from the open end of the sleeve. The closed end of the sleeve includes an outer surface having a mounting component thereon for mounting on a bone. An inner surface of the closed end cooperates with the piston to define an axially expandable pocket therebetween. Hydrogel is disposed within the pocket and is axially expandable relative to the axis defined by the chamber upon contact with fluid for forcing extension of the stem from the open end of the sleeve. A valve or metering pump controls the flow of the fluid to the hydrogel.

10 Claims, 3 Drawing Sheets

NON-INVASIVE EXPANDABLE PROSTHESIS FOR GROWING CHILDREN

TECHNICAL FIELD

The present invention relates to surgically implantable prostheses and, more particularly, is directed towards prostheses suitable for skeletal joints in juvenile patients. Such implants are adjustable as the patient grows.

BACKGROUND OF THE INVENTION

There are many types of surgically implantable prostheses available as substitute for natural bone and joints which have become damaged by disease or trauma. Practitioners have had high success in substituting by excising portions of the natural bone or joint and replacing such with a prosthesis.

A problem exists with presently available prostheses in the case of juveniles. As the patient grows, the limb having the prosthesis implanted typically does not grow at the same rate as the opposing limb. For example, it is not uncommon to find a patient having a prosthesis in a leg to have one leg shorter than the other.

In order to overcome the above-mentioned problem, adjustable length prosthetic joint implants have been developed. An example of such an implant is disclosed in U.S. patent application No. 4,502,160 to Moore, et al., issued Mar. 5, 1985 and assigned to the assignee of the present invention. The device disclosed in the Moore, et al. patent utilizes a threaded stem which can be extended from a barrel by a threaded nut mechanism. The stem is extended by exposure of a ratchet mechanism on the nut member which is rotated by a gear-carrying key. Use of such a system requires an incision of approximately two inches long which must be made each time an adjustment is desired. In other words, the use of such a device is invasive because each time an adjustment is made, access to the nut by the key member must be achieved. Since it is advisable for invasive surgery to be kept to a minimum, and a general anesthetic is necessary for such surgery for the adjustment of the length of the prosthesis, practitioners tend to overshoot the necessary extension at the time the post-operative expansion surgery is made to compensate for future growth. The extension causes stretching of ligaments and muscles to the extent that extensive rehabilitation is needed for the return of full range of motion of a joint. Further, since such devices are generally made out of titanium or titanium-alloy, and titanium surface wear properties are poor, the threaded portions of the device are susceptible to wear.

In view of the above problems, it is desirable to provide an adjustable length prosthesis which does not require an invasive element. That is, it is desirable to eliminate the post-operative surgery for expansion of the device. Additionally, it is desirable to eliminate the threads of the device. The present invention provides an adjustable length prosthetic implant requiring minimal or no post-operative surgery for expansion and does not require the use of a threaded stem element.

SUMMARY OF THE INVENTION

In accordance with the present invention, there is provided an adjustable length prosthetic implant including a stem having a rod portion. The rod portion has a first end portion adapted for implantation in a bone and a second end portion including a piston-sleeve combination. The sleeve includes a closed end and an inner chamber extending to an opposite open end, the inner chamber defining an axial dimension. The chamber contains the piston for sliding movement therethrough and extension of the first end portion of the stem from the open end of the sleeve. The closed end of the sleeve includes an outer surface having a mounting component thereon for mounting on another bone and an inner surface cooperating with the piston to define an axially expandable pocket therebetween. Axially expandable means is disposed within the pocket and is axially expandable relative to the axis defined by the chamber upon contact with the fluid for forcing extension of the stem from the open end of the sleeve. Valve means or a metering pump controls the flow of the fluid to the expandable means.

FIGURES IN THE DRAWINGS

Other advantages of the present invention will be readily appreciated as the same becomes better understood by reference to the following Detailed Description when considered in connection with the accompanying Drawings wherein.

DETAILED DESCRIPTION OF THE INVENTION

Figure 1:
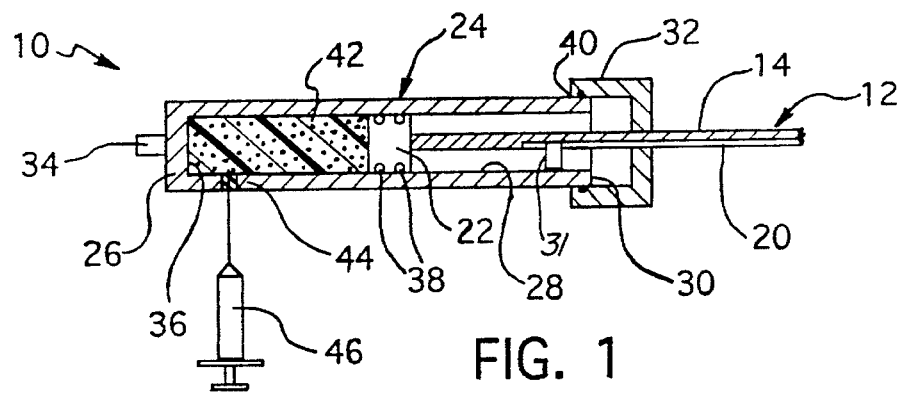
FIG. 1 is a cross-sectional side elevational view of a first embodiment of the present invention.
Figure 2:
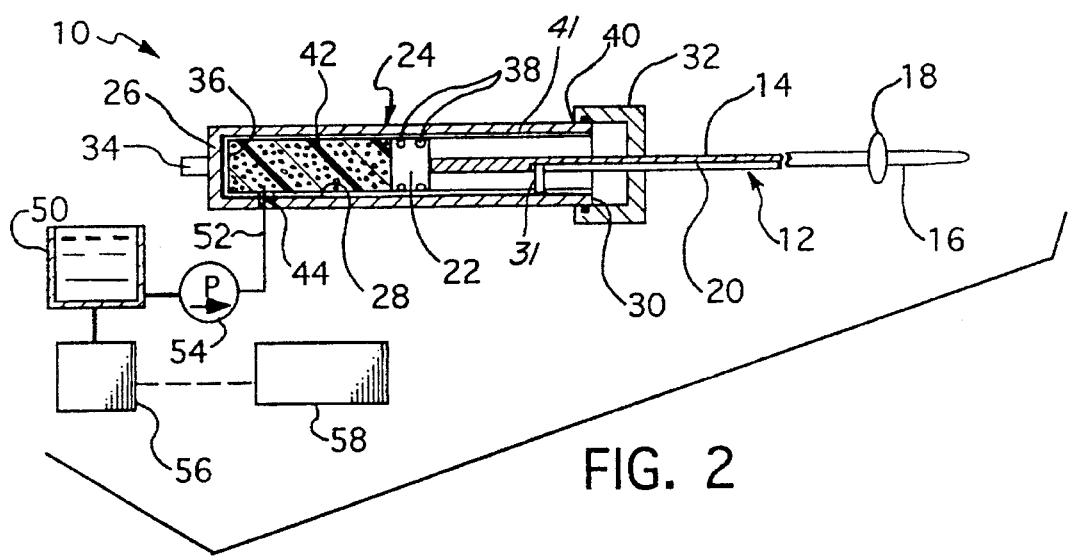
FIG. 2 is a cross-sectional side elevational view of a second embodiment of the present invention.
Figure 3:
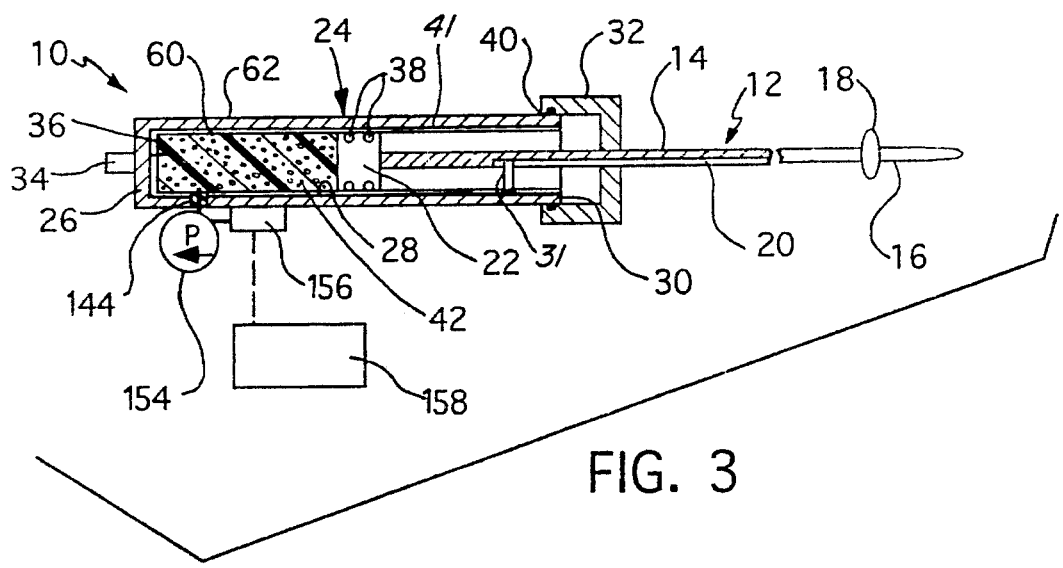
FIG. 3 is a cross-sectional side elevational view, partially broken away, of a third embodiment of the present invention.

An adjustable length prosthetic implant constructed in accordance with the present invention is generally shown at 10 in FIG. 1., like numbers being used between the several embodiments of the other FIGS. 2–6 to show like structure. The implant 10 includes a stem generally shown at 12 and including a rod portion 14 having a first end 16. As shown in FIGS. 2 and 3, the end 16 is adapted for connection to either a bone or a connecting means such as a taper for connection to other prosthetic components. For example, the end portion 16 can be a stem (or cylinder) or the like for implantation in the intramedullary canal of a femur for a femoral prosthesis, or a morse taper to allow multiple stem sizes. The end portion is preferably non-circular in cross-section to minimize the possibility of rotation after implantation. Such an end portion includes an intermediate collar portion 18 adjacent the end portion 16 which is adapted to overlie at least a portion of the severed bone to provide support therefor, and limiting proliferation of bone spurs which occasionally grow from amputated bone in juveniles. The stem 12 further includes a key-way type slot or groove 20 extending along at least a part of the length thereof for purposes described below. The stem 12 further includes a second end portion including a piston 22.

A barrel or sleeve generally shown at 24 includes a closed end 26 and an inner chamber 28 extending to an opposite open end 30. The chamber 28 defines an axial dimension extending the length thereof. The chamber 28 contains the piston 22 for sliding movement therethrough and extension of the first end portion 16 of the stem 12 from the open end 30 of the sleeve 24. A key 31 is supported on the sleeve 24 and extends radially inwardly and is positioned in the groove 20 for preventing relative rotation between the stem 12 and the sleeve 24. A nut member 32 can be disposed over the open end 30 to provide sealing engagement and assist guidance of the rod portion 14 of the stem member 12. Thus, the implant generally consists of a cylinder 24, piston rod 12, the piston rod including a piston 22 at the end thereof slidably moveable within the cylinder 24.

The closed end 26 of the sleeve 24 includes an outer surface having a mounting component 34 thereon for mounting on a bone. The mounting component can be in the form of an articulating component having condylar portions designed to articulate with the patella and a tibial component. Alternatively, the component 34 can be of the type adapted for an intercalary implant. Thus, the present invention could be used as a limb component or an articulating implant.

The closed portion 26 of the sleeve 24 also includes an inner surface 36 cooperating with the piston 22 to define an axially expandable pocket therebetween. In other words, as the piston moves through the chamber 28, an axially expanding pocket is defined between the closed end portion 36 and the piston 22.

The piston 22, as well as the nut member 32 and other connected joints, can include sealing means in the form of ring seals 38, 40 for perfecting fluid sealed joints. Also, as shown in FIG. 2, the sleeve 24 may include liner means 41 disposed within and about the chamber for decreasing frictional contact between the piston 22 and the barrel. The liner means 41 may take the form of a tubular polymer sleeve of, e.g., Teflon® (polytefrafluroethylene) interposed between the piston 22 and the sleeve 24. Although not show in the FIGS., the liner means 41 may be integrated into any of the following embodiments of the invention in identical fashion to that described above.

An axially expanding material 42 is disposed within the pocket defined between the end surface 36 and piston 22 and is axially expandable relative to the axis defined by the length of the chamber 28 upon contact with a fluid which is delivered to the pocket by a valve mechanism, schematically shown at 44, which controls the flow of the fluid to the expandable material 42. Rather than using a screw mechanism of the prior art to extend the stem 12 from the sleeve 24, the present invention includes a material which is axially expandable upon contact with the fluid, thereby obviating the need for a screw mechanism. As discussed below, expansion of the material can be controlled or metered either internally within the implant or by external means requiring minimal, e.g., hypodermic, invasion thereby obviating the need for periodic post-operative surgery and exposure to general anesthesia.

The preferred expandable material is a hydrogel contained within and filling the pocket of the sleeve 24. The wall of the sleeve prevents radial expansion of the hydrogel relative to the axis defined by the chamber 28 whereby incremental exposure of the hydrogel to fluid incrementally axially expands the hydrogel to incrementally extend the stem 12 from the open end 30 of the sleeve 24.

Hydrogels, or water containing gels, are lightly cross-linked polymers characterized by hydrophilicity and insolubility in water. In water, they swell to an equilibrium volume, but generally preserve their shape. The hydrophilicity is due to the presence of water solubilizing groups in the gel, such as hydroxyls, carboxyls, and the like. The insolubility and stability of shape are due to the presence of a three-dimensional network. The swollen state results from a balance between the dispersing forces acting on hydrated chains and the cohesive forces that do not prevent the penetration of water into the network.

Examples of hydrogels are hydrogels based on methacrylic and acrylic esters, acrylamide hydrogels, hydrogels based on N-vinyl-2-pyrrolidinone, polyelectrolyte complexes and charged hydrogels, charged composite hydrogels, covalently cross-linked polyelectrolyte networks, polyvinyl alcohols, as well as other type of hydrogels.

The most important property of hydrogels is the ability to imbibe water. The resulting osmotic swelling is generally opposed by the elastic contractility of the stretched hydrogen network.

The present invention utilizes a dehydrated hydrogel shaped to fill the pocket defined between the inner surface 36 of the end portion 26 of the sleeve 24 and the piston 22 filling the chamber or pocket therebetween. Upon selective hydration of the hydrogel, the only direction of expansion not restricted is axial expansion which forces the piston 22 to move through the chamber 28 away from the end surface 36 which extends the stem 12 from the sleeve 24. By controlling or metering water-based fluids, e.g., saline, into the pocket containing hydrogel, the increase in length of the implant is controlled and can be made to substantially reflect physiological growth in the patient.

Referring specifically to the first embodiment shown in FIG. 1, the valve 44 is a simple one-way valve which can be in the form of a puncturable membrane. A syringe 46 can be used to periodically inject fluid into the pocket for expanding the hydrogel 42. Such an embodiment would require minimum invasion, i.e., require no bodily incision.

A second embodiment of the invention is shown in FIG. 2. This embodiment, as well as the embodiment shown in FIG. 3, includes metering means for metering the flow of fluid through the valve 44, controlling the amount and rate of extension of the stem 12 from the sleeve 24. The embodiment shown in FIG. 2 includes an external fluid reservoir 50 which can be in the form of an implantable membrane pocket or the like. The reservoir 50 is in fluid communication through tubing 52 with the pocket of the sleeve through the valve 44. The valve 44 is a one-way valve allowing fluid flow from the reservoir 50 to the pocket.

The metering mechanism includes a pump 54 in fluid communication between the reservoir 50 and the valve 44 and an electronic control mechanism 56 for controlling activity of the pump 54 to control the amount and rate of fluid pumped therethrough. More specifically, the electronic control mechanism 56 includes a central processing unit (CPU) for providing a pre-programmed, or preset, movement of fluid to the hydrogel 42. The program stored in the CPU would control both the duration and initiation of pump 54 operation. Thus, the electronic control mechanism 56 is preset for metering fluid flow to be consistent with growth of the opposing limb.

However, in the event the preprogrammed metered fluid flow dosage must be increased or decreased to account for an unanticipated opposing bone growth rate, the electronic control mechanism 56 can be fitted with a radio wave receiver such as is well known for use in conjunction with electronic metering devices for implanted insulin pumps in diabetic patients. Such a metering device can be controlled telemetrically by an electronic transmitter 58 thereby providing a prosthesis which requires absolutely no post-surgery invasion, i.e., a non-invasive expandable prosthesis. The radio-wave receiver attached to the electronic control mechanism 56 is responsive to signals generated by the electronic transmitter 58 for adjusting the duration and/or activation of the pump 54 into conformity with the actual rate of bone growth in the opposing limb. Thus, at least semi-continuous growth can be mimicked by the adjustable length prosthetic implant. Such growth eliminates the need for over-extension of the prosthesis length during initial implantation, thereby minimizing the need for rehabilitation for the return of full range motion due to such over-extension.

A third embodiment of the invention is shown in FIG. 3 wherein the sleeve 24 includes an inner wall 60 and an outer wall 62 spaced from the inner wall 60 and defining a reservoir therebetween. Fluid is contained within the reservoir, with the valve 144 controlling fluid flow from the reservoir to the pocket containing the hydrogel 42. The control mechanism includes an electronic metering receiver 156, similar to those discussed above, mounted directly on the sleeve 24 and operatively connected to the pump 154 and a remote control transmitter 158 similar to those discussed above for remotely, or telemetrically, communicating with the metering receiver 156 to non-invasively control the extension of the stem 12 by remotely controlling fluid flow to the pocket from the internal reservoir. As compared to the embodiment of FIG. 2, this third embodiment provides a much more compact prosthesis wherein the reservoir may contain sufficient water to allow for a complete expansion of the stem 12 during the growth of the child. Alternatively, both the reservoir 50 shown in FIG. 2 and the internal reservoir shown in FIG. 3 between walls 60 and 62 can be made accessible through injection of further water-based fluid, such as by a hypodermic needle through a membrane as shown for valve 44 in FIG. 1.

Figure 4:
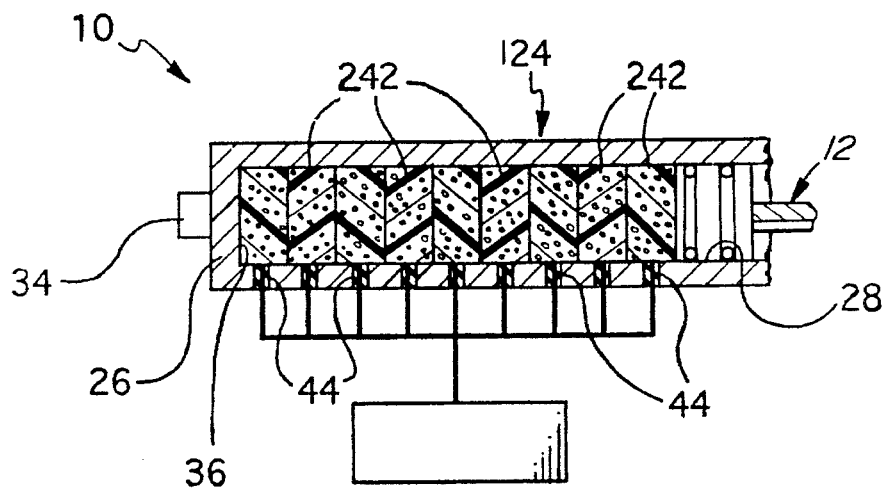
FIG. 4 is a cross-sectional side elevational view, partially broken away, of a fourth embodiment of the present invention.
Figure 4A:
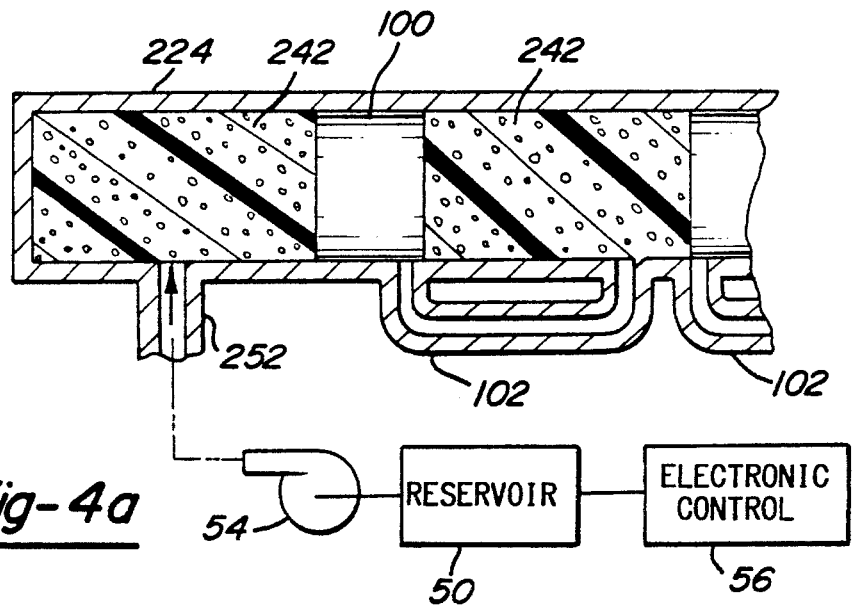
FIG. 4a is an enlarged fragmentary view of the first two hydrogel discs as in FIG. 4.
Figure 4B:
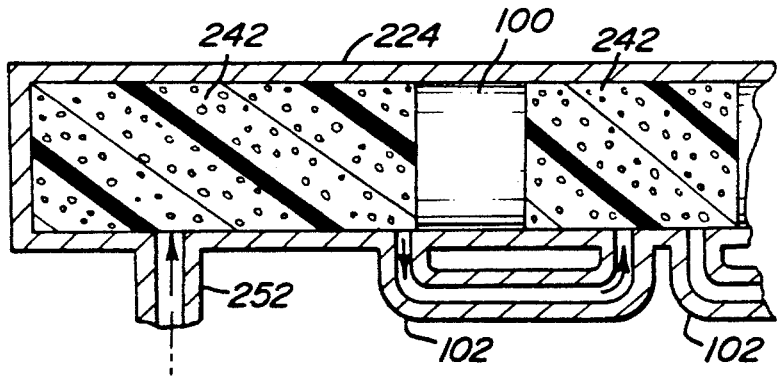
FIG. 4b is a view as in FIG. 4a showing the first hydrogel disc fully expanded.

FIG. 4 shows a further embodiment of the invention wherein the hydrogel material is in the form of a plurality of discs 242. FIGS. 4a and 4b illustrate in simplified schematic fashion a valving and isolator plate arrangement for expanding the several hydrogel discs 242 one at a time. In FIG. 4a, the rear end of the sleeve 224 is shown in fragmentary cross-sectional fashion with first and second hydrogel discs 242 disposed therein. A plurality of interleaved isolator discs 100, fabricated from a non-fluid permeable and nonexpanding material, such as a metal or polymer, are disposed between the hydrogel discs 42. The inlet tube 252 directs fluid from the pump 54 into direct contact with the first hydrogel disc 242. However, the first isolator disc 100 establishes a fluid impervious barrier between the first and second hydrogel discs 242 so that fluid entering through the inlet tube 252 is not permitted to contact the second isolator disc 242.

As shown in FIG. 4b, fluid introduced to the first hydrogel disc 242 expands the first hydrogel disc 242 in the sleeve 24 thus axially displacing the entire stack of hydrogel discs 242 and ultimately the stem 12. Such axial movement causes the first isolator disc 100 to move axially within the sleeve 224 to the position shown in FIG. 4b. Thus, when the first hydrogel disc 242 is fully saturated, the first isolator disc 100 opens a bypass tube 102 permitting fluid to flow therethrough and contact and expand a second hydrogel disc 242. In this manner, a series of isolator discs 100 and bypass tubes 102 are formed along the length of the sleeve 224 so that the hydrogel discs 242 are individually exposed to fluid in sequential fashion.

Of course, other valving arrangements to the hydrogel discs 242" are possible. For example, each hydrogel disc 242" may be encapsulated within a polymer bag (not shown), with a fluid porting system arranged in "parallel flow" fashion to introduce fluid to the hydrogel discs 242" individually.

Figure 5:
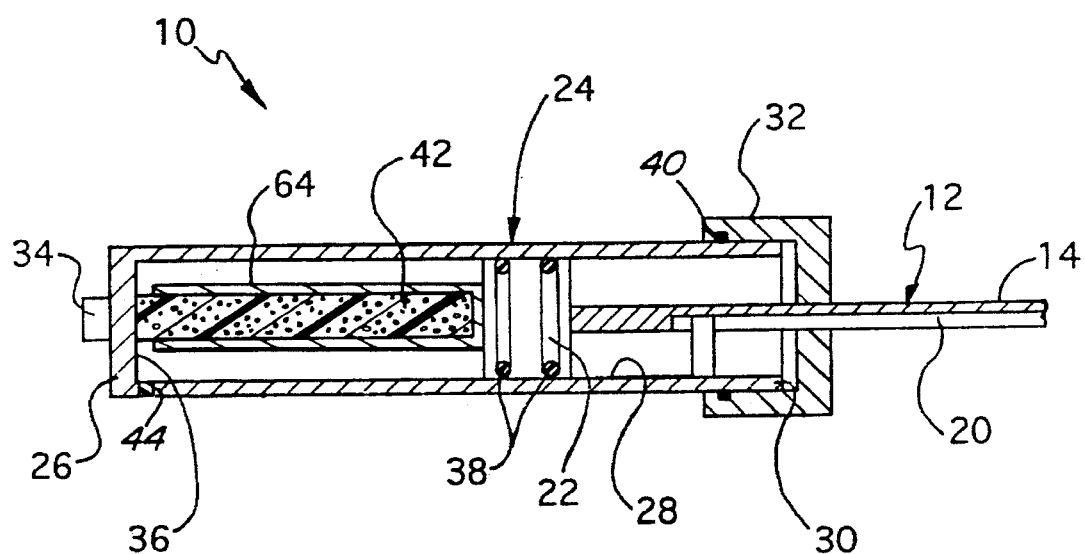
FIG. 5 is a fragmentary, cross-sectional side elevational view of a fifth embodiment of the present invention.
Figure 6:
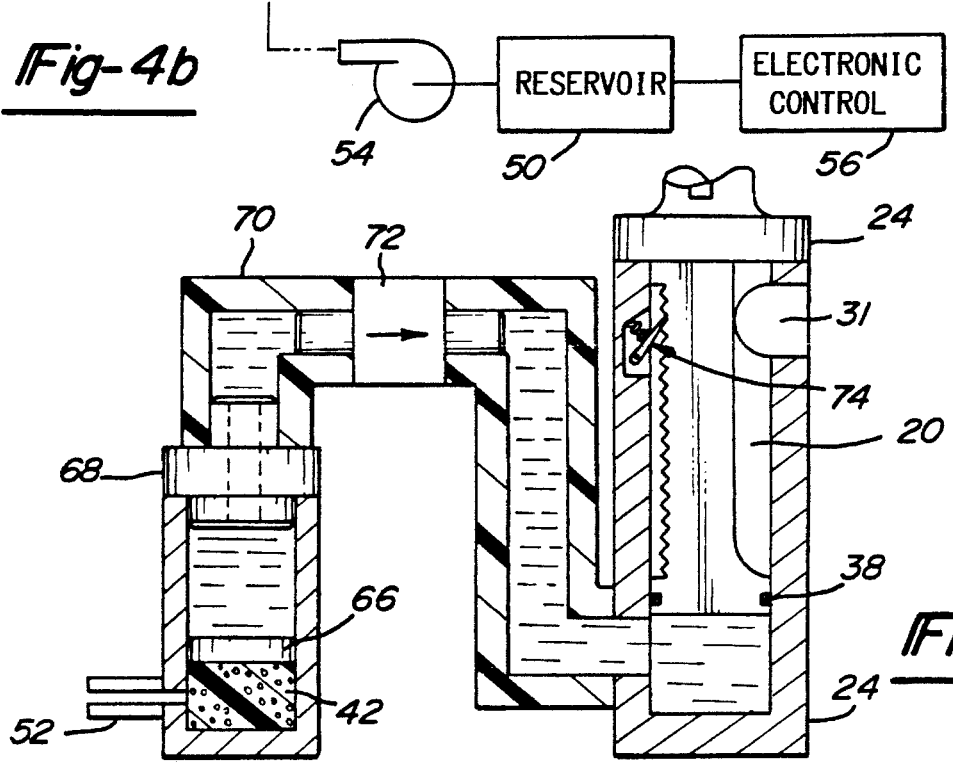
FIG. 6 is a simplified schematic view of the invention as in FIG. 5.

FIG. 5 shows a further embodiment of the invention wherein the hydrogel 42 is contained within a secondary telescoping pocket having an inner wall 64. In this embodiment, the hydrogel material is placed within a secondary chamber defined by the telescoping wall 64 to gain a hydraulic advantage over direct hydrogel contact. FIG. 6 shows an embodiment wherein the hydrogel 42 is disposed contiguous a piston 66 within the secondary chamber. A connector piece 68 connects the secondary chamber to an intermediate tube 70 which, in turn, is operatively connected to the sleeve 24. A check valve 72 is disposed within the intermediate tube 70 for allowing fluid flow in only one direction, i.e., from the secondary chamber to the sleeve 24. The secondary chamber, intermediate tube 70, and the sleeve 24 are filled to capacity with an essentially incompressible hydraulic fluid for transmitting movement of the piston 66 to the stem 12.

According to this embodiment shown in FIG. 6, the diameter of the piston 66 is smaller than the diameter of the stem 12 to obtain the hydraulic advantage referred to above. Thus, for example, if the diameter of the piston 66 is 0.200 inches and given that expansion of the hydrogel 42 creates a 100 pound axial force, the well known formula F=PA can be applied as follows, where:

F=Force
P=Pressure
A=Area $$F=PA$$

100 lbs.=P $((0.200)^2 \pi)$
100 lbs.=(0.12566 in.$^2$) P
P=795.798 psi

Accordingly, expansion of the hydrogel 42 creates a static pressure in the secondary chamber, intermediate tube 70 and sleeve 24 of 795.798 psi. Therefore, applying the same equations as above and given a stem 24 diameter of 0.350 inches, the force transmitted to the stem 12 is determined as follows:

F=PA
F=795.798 $((0.350)^2 \pi)$
F=306.25 lbs.

Also, as shown in simplified form in FIG. 6, a ratchet mechanism 74 may be disposed between the sleeve 24 and the stem 12 for preventing excessive compressive forces on the stem 12 from damaging the check valve 72 or other components of the system. This ratchet system could, of course, be integrated into any one of the preceding embodiments to accomplish the same goal.

Each of the above embodiments provides at least a minimally-invasive device which can grow, but can do so without any incisions made in the patient. Furthermore, the rate of expansion can be readily controlled by internal electronics and altered at any time by external electronic control to the extent it is non-invasive.

The invention has been described in an illustrative manner, and it is to be understood that the terminology which has been used is intended to be in the nature of words of description rather than of limitation.

Obviously many modifications and variations of the present invention are possible in light of the above teachings. It is, therefore, to be understood that within the scope of the appended claims, the invention may be practiced otherwise than as specifically described.

What is claimed is:

1. An adjustable length prosthetic implant comprising:
   a stem including a rod portion having a first end portion adapted for connection to a base end and a second end portion including a piston, said base end being shaped, sized and configured to be connected to a group consisting of a bone and a bone prosthesis;
   a sleeve including a closed end and an inner chamber extending to an opposite open end and defining an axial dimension, the chamber containing the piston for sliding movement therethrough and extension of the first end portion of the stem from the open end of the sleeve, the closed end including an outer surface having a mounting component thereon for mounting on a base and an inner surface cooperating with the piston to define an axially expandable pocket therebetween;
   axially expandable means disposed within the pocket and axially expandable relative to the axis defined by the chamber upon contact with a fluid for forcing extension of the stem from the open end of the sleeve; the axially expandable means being hydrogel which expands upon contact with the fluid; and
   valve means for controlling the flow of the fluid to the expandable means.

2. An adjustable length prosthetic implant comprising:
   a stem including a rod portion having a first end portion adapted for connection to a base end and a second end portion including a piston; the base end being shaped, sized and configured to be connected to a group consisting of a bone and a bone prosthesis;
   a sleeve including a closed end and an inner chamber extending to an opposite open end and defining an axial dimension, the chamber containing the piston for sliding movement therethrough and extension of the first end portion of the stem from the open end of the sleeve, the closed end including an outer surface having a mounting component thereon for mounting on a base and an inner surface cooperating with the piston to define an axially expandable pocket therebetween;
   axially expandable means disposed within the pocket and axially expandable relative to the axis defined by the chamber upon contact with a fluid for forcing extension of the stem from the open end of the sleeve;
   valve means for controlling the flow of the fluid to the expandable means; and
   metering means for metering flow through the valve means and controlling the amount and rate of extension of the stem from the sleeve.

3. A prosthetic implant as set forth in claim 2 including an external reservoir of the fluid in fluid communication with the pocket through the valve means, the valve means including a one way valve allowing fluid flow from the reservoir to the pocket, the metering means including a pump in fluid communication between the reservoir and the valve and control means for controlling activity of the pump to control the amount and rate of fluid pumped therethrough.

4. A prosthetic implant as set forth in claim 3 wherein the sleeve includes an inner wall and an outer wall spaced from the inner wall and defining the reservoir therebetween.

5. A prosthetic implant as set forth in claim 3 wherein the control means includes an electronic metering receiver mounted on the sleeve and operatively connected to the pump and a remote control transmitter for remotely communicating with the metering receiver to non-invasively control the extension of the stem by remotely controlling fluid flow to the pocket of the sleeve.

6. An adjustable length prosthetic implant comprising:
   a stem including a rod portion having a first end portion adapted for connection to a base end and a second end portion including a piston; the base end being shaped, sized and configured to be connected to a group consisting of a bone and a bone prosthesis;
   a sleeve including a closed end and an inner chamber extending to an opposite open end and defining an axial dimension, the chamber containing the piston for sliding movement therethrough and extension of the first end portion of the stem from the open end of the sleeve, the closed end including an outer surface having a mounting component thereon for mounting on a base and an inner surface cooperating with the piston to define an axially expandable pocket therebetween;
   axially expandable means disposed within the pocket and axially expandable relative to the axis defined by the chamber upon contact with a fluid for forcing extension of the stem from the open end of the sleeve; and
   valve means for controlling the flow of the fluid to the expandable means;
   wherein the expandable means is a hydrogel contained within and filling the pocket, the sleeve preventing radial expansion of the hydrogel relative to the axis defined by the chambers whereby incremental exposure of the hydrogel to water incrementally axially expands the hydrogel to incrementally extend the stem from the open end of the sleeve.

7. A prosthetic implant as set forth in claim 6 wherein the hydrogel is a rod-shaped member.

8. A prosthetic implant as set forth in claim 6 wherein the hydrogel is arranged as a series of discs, the pocket containing the series of the discs.

9. An adjustable length prosthetic implant comprising:
   a stem including a rod portion having a first end portion adapted for connection to a base end and a second end portion including a piston; the base end being shaped, sized and configured to be connected to a group consisting of a bone and a bone prosthesis;
   a sleeve including a closed end and an inner chamber extending to an opposite open end and defining an axial dimension, the chamber containing the piston for sliding movement therethrough and extension of the first end portion of the stem from the open end of the sleeve, the closed end including an outer surface having a mounting component thereon for mounting on a base and an inner surface cooperating with the piston to define an axially expandable pocket therebetween;
   axially expandable means disposed within the pocket and axially expandable relative to the axis defined by the chamber upon contact with a fluid for forcing extension of the stem from the open end of the sleeve;
   valve means for controlling the flow of the fluid to the expandable means;
   wherein the expandable means is a hydrogel contained within and filling the pocket, the sleeve preventing radial expansion of the hydrogel relative to the axis defined by the chambers whereby incremental exposure of the hydrogel to water incrementally axially expands the hydrogel to incrementally extend the stem from the open end of the sleeve;

wherein the hydrogel is arranged as a series of discs, the pocket containing the series of the discs; and flow control means for controlling fluid flow to each of the disc-shaped members to control the rate of extension of the stem from the open end of the sleeve.

10. An adjustable length prosthetic implant comprising:

a stem including a rod portion having a first end portion adapted for connection to a base end and a second end portion including a piston; the base end being shaped, sized and configured to be connected to a group consisting of a bone and a bone prosthesis;

a sleeve including a closed end and an inner chamber extending to an opposite open end and defining an axial dimension, the chamber containing the piston for sliding movement therethrough and extension of the first end portion of the stem from the open end of the sleeve, the closed end including an outer surface having a mounting component thereon for mounting on a base and an inner surface cooperating with the piston to define an axially expandable pocket therebetween;

axially expandable means disposed within the pocket and axially expandable relative to the axis defined by the chamber upon contact with a fluid for forcing extension of the stem from the open end of the sleeve; and valve means for controlling the flow of the fluid to the expandable means; and liner means disposed about the chamber for decreasing frictional contact between the piston and the barrel.

* * * * *